(12) United States Patent
Jansen-Troy

(10) Patent No.: US 10,143,508 B2
(45) Date of Patent: Dec. 4, 2018

(54) TOOL DEVICE, IN PARTICULAR HAND-HELD TOOL DEVICE, FEATURING TORQUE LIMITATION

(71) Applicant: SMC Innovation GmbH, Cham (CH)

(72) Inventor: Arne Jansen-Troy, Stockach (DE)

(73) Assignee: SMC INNOVATION GMBH, Cham (CH)

( * ) Notice: Subject to any disclaimer, the term of this patent is extended or adjusted under 35 U.S.C. 154(b) by 71 days.

(21) Appl. No.: 15/129,931

(22) PCT Filed: Apr. 1, 2015

(86) PCT No.: PCT/EP2015/057232
§ 371 (c)(1),
(2) Date: Sep. 28, 2016

(87) PCT Pub. No.: WO2015/155097
PCT Pub. Date: Oct. 15, 2015

(65) Prior Publication Data
US 2017/0020591 A1   Jan. 26, 2017

(30) Foreign Application Priority Data
Apr. 9, 2014   (DE) .................. 10 2014 105 078

(51) Int. Cl.
*A61B 17/88*   (2006.01)
*B25B 23/14*   (2006.01)
(Continued)

(52) U.S. Cl.
CPC .......... *A61B 17/8875* (2013.01); *A61B 90/03* (2016.02); *B25B 15/02* (2013.01);
(Continued)

(58) Field of Classification Search
CPC .... B25B 23/14; B25B 23/145; B25B 23/1427
(Continued)

(56) References Cited

U.S. PATENT DOCUMENTS 5,735,854 A * 4/1998 Caron ................ A61B 17/8875
606/104
6,308,598 B1 * 10/2001 O'Neil .............. A61B 17/8875
81/439

(Continued)

OTHER PUBLICATIONS

International Search Report & Written Opinion of the International Searching Authority dated Jun. 23, 2016 issued in corresponding International Patent Application No. PCT/EP2015/057232 (and partial English translation).

(Continued)

*Primary Examiner* — Nicholas Woodall
(74) *Attorney, Agent, or Firm* — Posz Law Group, PLC

(57) ABSTRACT

The invention is based on a tool device, in particular hand-held tool device, for use in a surgical method, comprising a tool receptacle, an operating unit, a torque limitation unit, a torque transmission unit and a magazine unit. The torque limitation unit is arranged between the operating unit and the tool receptacle and comprises a plurality of torque limitation elements which are provided to be destroyed when a given torque is exceeded. The magazine unit is provided to exert a thrust force onto the torque limitation elements for introducing them one by one into the torque transmission unit, and the torque limitation unit is provided to respectively receive a torque limitation element and to destroy it when the given torque is exceeded, wherein the torque limitation elements are arranged on a rotary working axle of the tool receptacle.

20 Claims, 3 Drawing Sheets

Figure 1:
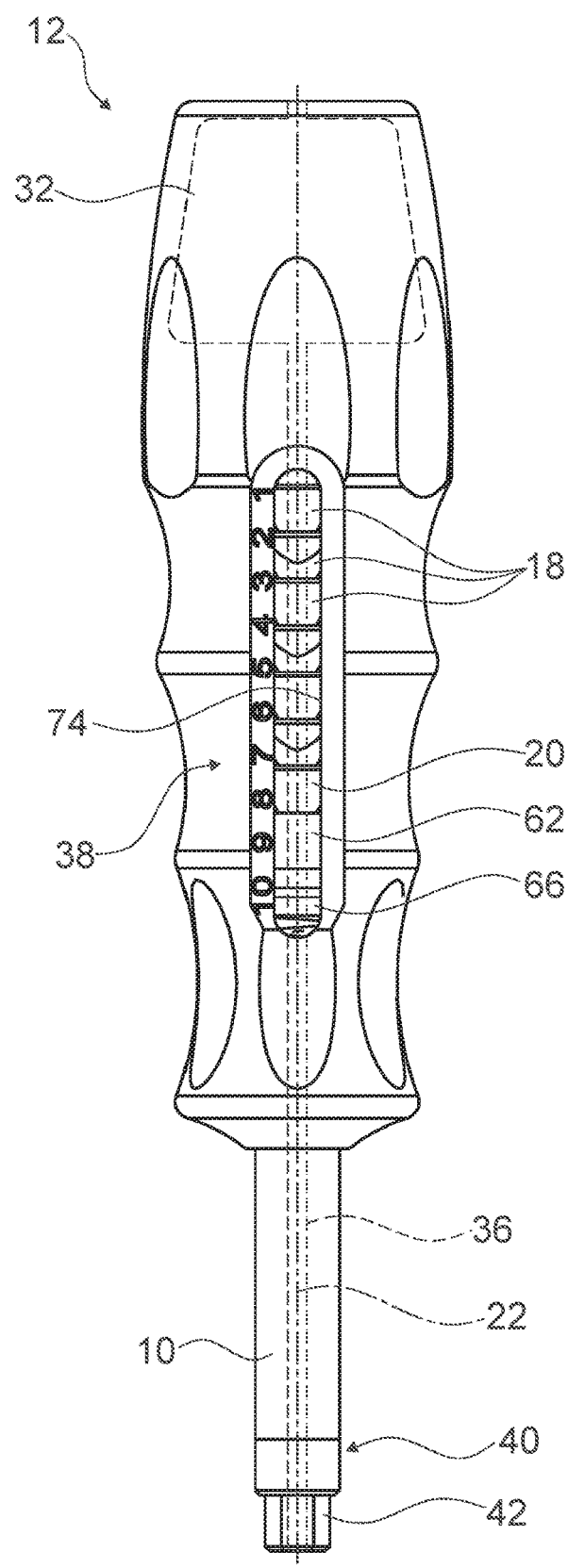

(51) Int. Cl.
 *B25B 15/02* (2006.01)
 *B25B 23/142* (2006.01)
 *A61B 90/00* (2016.01)

(52) U.S. Cl.
 CPC ...... *B25B 23/1415* (2013.01); *B25B 23/1427* (2013.01); *A61B 2090/031* (2016.02); *A61B 2090/037* (2016.02)

(58) Field of Classification Search
 USPC .......................................................... 81/467
 See application file for complete search history.

(56) References Cited

U.S. PATENT DOCUMENTS

2008/0016990 A1  1/2008  Rinner
2009/0266204 A1  10/2009  Rinner

OTHER PUBLICATIONS

German Search Report dated Jan. 30, 2015 in the corresponding DE application No. 10 2014 105 078.9. ( Partial english translation attached).

\* cited by examiner

TOOL DEVICE, IN PARTICULAR HAND-HELD TOOL DEVICE, FEATURING TORQUE LIMITATION

CROSS REFERENCE TO RELATED APPLICATIONS

This application is a U.S. national stage application of PCT/EP2015/057232 filed on Apr. 1, 2015, which claims priority to German Patent Application No. DE102014105078.9 filed on Apr. 9, 2014, the contents of which are incorporated herein by reference.

STATE OF THE ART

The invention relates to a tool device, in particular a hand-held tool device, for use in a surgical method according to patent claim 1.

As described in US 2008/0016990 A1 a tool device for use in a surgical method, comprising a tool receptacle, an operating unit and a torque limitation unit with at least one torque limitation element, is already known, the torque limitation unit being arranged between the operating unit and the tool receptacle.

In the field of medicine, in particular during a surgical procedure, there are high demands regarding an accuracy of tool devices. This concerns, among others, a maximum torque with which, for example, screws are screwed in.

The objective of the invention is in particular to provide a generic tool device featuring increased accuracy. The objective is achieved according to the invention by the features of patent claim 1, while advantageous embodiments and further implementations of the invention may be gathered from the subclaims.

ADVANTAGES OF THE INVENTION

The invention is based on a tool device, in particular hand-held tool device, for use in a surgical method, comprising a tool receptacle, an operating unit and a torque limitation unit with at least one torque limitation element, the torque limitation unit being arranged between the operating unit and the tool receptacle.

According to the invention, it is proposed that the at least one torque limitation element is provided to be destroyed when a given torque is exceeded. Thus a torque transmission is interruptible in a particular secure manner when the given torque is exceeded. A "tool receptacle" is to be understood, in this context, in particular as an element of the tool device which is provided to hold an insert tool in a torsionally stable fashion. Preferably the tool receptacle is provided to receive the insert tool from an operator in such a way that it is re-releasable. An "operating unit" is to be understood, in this context, in particular as a unit which is provided to be operated by a user of the tool device. The operating unit advantageously comprises at least one handle. In this context it is conceivable that the operating unit comprises a T-handle piece. A "torque limitation unit" is to be understood, in this context, in particular as a unit provided for a limitation of a torque that is to be transmitted. Advantageously the torque limitation unit decouples a torque transmission between the operating unit and the tool receptacle when a pre-set torque is exceeded. The at least one torque limitation element may be implemented of ceramics, metal or preferentially of a plastics material. By "destroy" is to be understood, in this context, in particular to separate off from the neighboring torque limitation element or from a neighboring guiding element. By "provided" is to be understood, in particular, specifically programmed, designed and/or equipped. By an object being provided for a certain function is in particular to be understood that the object fulfills and/or implements said certain function in at least one application state and/or operating state.

In a further implementation of the tool device it is proposed that the torque limitation unit is provided to irreversibly interrupt a torque transmission between the operating unit and the tool receptacle following a limited number of torque excess events. This allows ensuring disposal of the tool device following a limited number of torque excess events. A re-use of the tool device following the limited number of torque excess events is advantageously avoidable. A health risk due to use of a contaminated tool device is particularly advantageously reducible. The term "following a limited number" is to mean, in this context, in particular following one event, preferably following maximally five events, especially advantageously following maximally ten events.

According to the invention, it is further proposed that the at least one torque limitation element is arranged on a rotary working axle of the tool receptacle. This allows implementing the tool device in a particularly compact fashion. By a "rotary working axle" is to be understood, in this context, in particular an axle about which the tool receptacle and/or advantageously the tool device is rotated in an operation mode, in particular when screwing or unscrewing a screw. Advantageously a center of mass of the at least one torque limitation element is located on the rotary working axle or apart from the rotary working axle by a distance of less than 5 mm, preferably less than 2 mm, particularly preferably less than 1 mm.

According to the invention, it is moreover proposed that the torque limitation unit comprises a plurality of torque limitation elements which are provided to be destroyed when a given torque is exceeded. In this way a limited number of possible torque excess events can be set in an error-proof manner.

The tool device may be implemented in a particularly compact fashion if the torque limitation elements are embodied in a one-part implementation with each other. "Embodied in a one-part implementation" is to mean in particular at least connected by substance-to-substance bond, e.g. by a welding process, an adhesive-bonding process, an injection-molding process and/or by another process that is deemed expedient by the person having ordinary skill in the art, and/or advantageously formed in one piece, e.g. by production from one cast, from a single blank and/or advantageously by production in a one-component or multi-component injection-molding process.

According to the invention, if the tool device comprises a torque transmission unit which is provided to respectively receive and, when the given torque is exceeded, destroy a torque limitation element, a structurally simple torque limitation is achievable. By a "torque transmission unit" is in particular, in this context, a unit to be understood which in at least one operation mode transmits a torque from an operating unit to a tool receptacle. The torque transmission unit is advantageously provided to exert in a torque transmission a force onto the torque limitation element.

It is also proposed that the torque transmission unit is provided to destroy respectively one torque limitation element by a torsion. As a result of this, particularly reliable destruction of the torque limitation element is achievable when there is a preset torque. As an alternative, it is also conceivable to respectively destroy a torque limitation element via exertion of a shear force.

According to the invention, it is furthermore proposed that the tool device comprises a magazine unit which is provided to exert a thrust force onto the torque limitation elements for introducing them one by one into a torque transmission unit. In this way, a semi-automatic or automatic loading of the torque transmission unit with the at least one torque limitation element can be effected in an operation mode. Preferably the magazine unit comprises at least one compression spring provided to exert the thrust force onto the at least one torque limitation element. Advantageously the compression spring is embodied of nitinol.

An especially precise torque limitation is achievable if the magazine unit comprises a compensation unit which is provided to keep the thrust force at least substantially constant for each of the torque limitation elements. By a "compensation unit" is to be understood, in this context, in particular a unit comprising a spring-setting unit and/or advantageously a friction-setting unit. By a "spring-setting unit" is to be understood, in this context, in particular a unit provided to set a spring force of the compression spring. Preferentially the spring-setting unit is provided to set a length of the compression spring. Advantageously the spring-setting unit comprises at least one thread element which is provided to abut the compression spring. By a "friction-setting unit" is to be understood, in this context, in particular a unit provided to set a friction force between the at least one torque limitation element and the torque transmission unit, in particular depending on a spring force.

Loss of destroyed torque limitation elements is avoidable if the operating unit comprises at least one receiving chamber which is provided to receive at least one destroyed torque limitation element of the torque limitation unit. Preferably the receiving chamber is delimited by two operating parts of the operating unit.

It is further proposed that the operating unit comprises at least one operating part for the purpose of forming a receiving space in which the torque limitation unit is arranged in an assembled state. Advantageously the operating part is embodied in such a way that a non-destructive access to the receiving space is avoided. By an "access" is, in this context, in particular a free opening to be understood that allows introducing a hand, a finger/fingers and/or a tool into the receiving space. The operating part advantageously does not comprise any access with a maximum opening diameter of more than 3 mm.

Preferentially the operating unit comprises two operating parts. Advantageously the operating unit comprises a latch unit which is provided to latch the two operating parts.

If the tool device comprises a pass-through channel penetrating the tool receptacle, the operating unit and the torque limitation unit at least to a major part, advantageously a Kirschner wire and/or any guiding wire may be received. Advantageously the pass-through channel has a diameter of less than 3 mm, preferably less than 1 mm. Preferably the pass-through channel penetrates the tool receptacle, the operating unit, the torque limitation unit and the at least one torque limitation element completely. Especially advantageously the pass-through channel has a round cross-section. Further advantageously a symmetry axis of the pass-through channel corresponds to the rotary working axle of the tool receptacle.

It is moreover proposed that the tool device comprises a filling level indication unit which is provided to indicate a remaining number of torque limitation elements. By a "filling level indication unit" is, in this context, in particular a unit to be understood which is provided to acoustically and/or preferably optically indicate a number of remaining torque limitation elements. Additionally or alternatively the filling level indication unit is provided to indicate already used-up torque limitation elements.

Furthermore a method is proposed for limiting a torque of a tool device comprising a tool receptacle and an operating unit, with an operator applying a torque onto the tool receptacle via the operating unit and a torque limitation unit, wherein, at a given torque, at least one torque limitation element of the torque limitation unit is destroyed. In this way a torque transmission is particularly securely interruptible when the given torque is exceeded.

It is further proposed that, following a pre-determinable number of torque excess events, a torque transmission between the operating unit and the tool receptacle is irreversibly interrupted. This allows ensuring a disposal of the tool device following a limited number of torque excess events. A re-use of the tool device following the limited number of torque excess events is advantageously avoidable. A health risk due to using a contaminated tool device is thus reducible in an especially advantageous manner.

DRAWINGS

Further advantages may be gathered from the following description of the drawings. The drawings show an exemplary embodiment of the invention. The drawings, the description and the claims contain a plurality of features in combination. The person having ordinary skill in the at will purposefully also consider the features individually and will find further expedient combinations.

Figure 2:
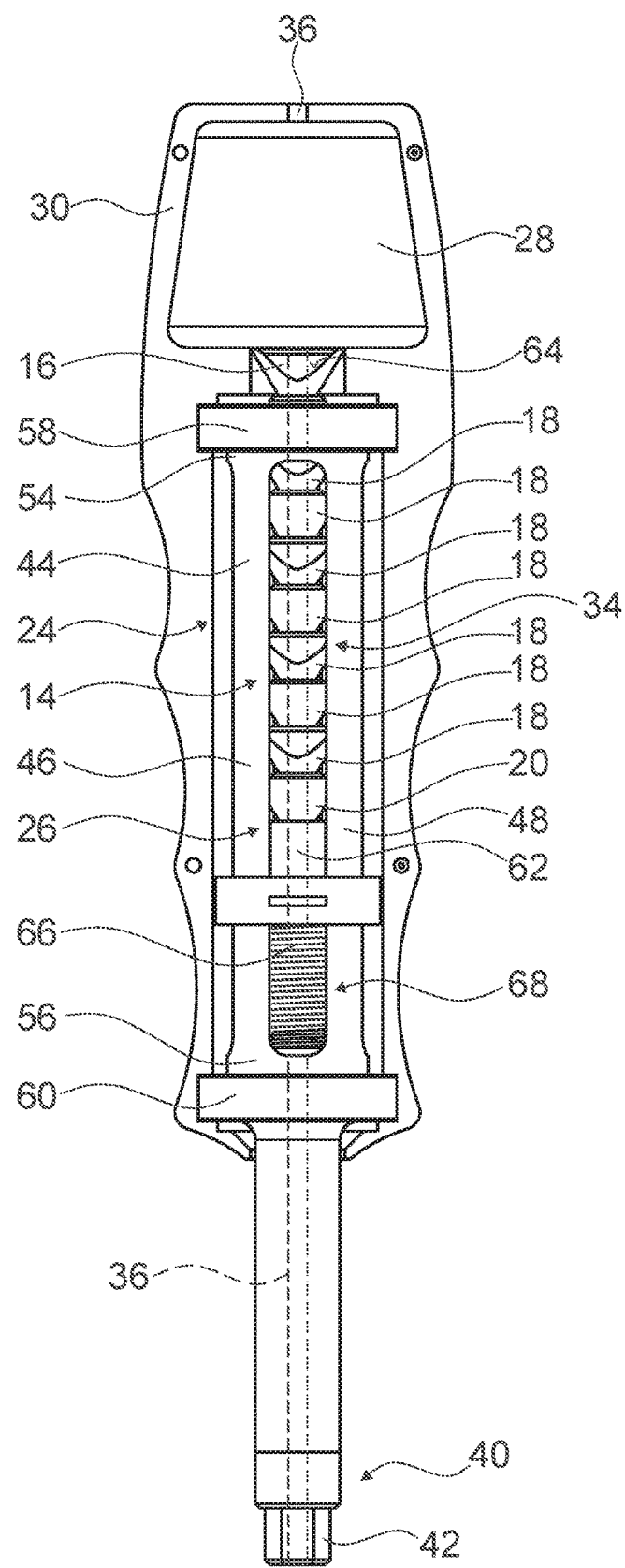
Figure 3:
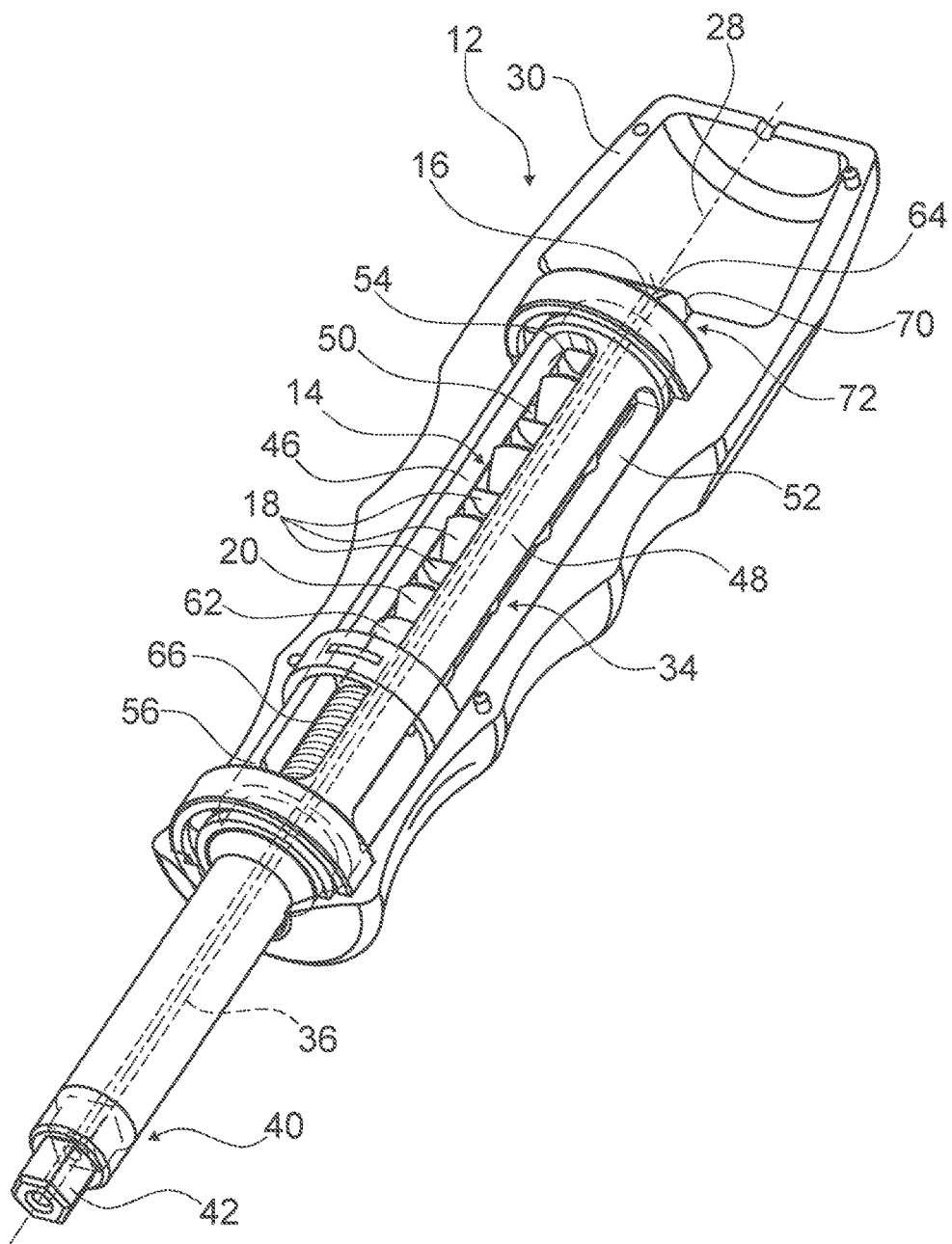

It is shown in:

FIG. 1 a lateral view of a tool device,

FIG. 2 a lateral view of the tool device with only one operating element, and FIG. 3 a perspective partial section through the tool device.

DESCRIPTION OF THE EXEMPLARY EMBODIMENT

FIGS. 1 to 3 show a tool device that is implemented as a hand-held tool device. The tool device is provided to be used in a surgical method. The tool device comprises a tool receptacle 10. The tool receptacle 10 is releasably coupled to an insert tool 42 at a free end 40. The tool receptacle 10 is provided to hold the insert tool 42 in a torsionally stable manner. Herein the insert tool 42 is exchangeable by an operator. The insert tool 42 is embodied as a hexagon bit. Thus the insert tool 42 is complementary in shape to an inner hexagon of a (not shown) screw. Principally it is also conceivable that the tool receptacle 10 is itself provided to be coupled with a screw in a torsionally stable manner. In a work process the tool device rotates about a rotary working axle 22 of the tool receptacle 10.

The tool device further comprises a magazine unit 24. The magazine unit 24 comprises a receiving frame 44. The receiving frame 44 is provided to receive a torque limitation unit 14 of the tool device. The receiving frame 44 comprises four holding rods 46, 48, 50, 52. The holding rods 46, 48, 50, 52 extend in a main extension direction parallel to the rotary working axle 22 of the tool receptacle 10. The holding rods 46, 48, 50, 52 are connected to each other on free lengthwise ends. The magazine unit 24 comprises for this purpose an upper closure part 54 and a lower closure part 56. The upper closure part 54 and the lower closure part 56 are provided for connecting the holding rods 46, 48, 50, 52. The upper closure part 54 has a circular outer contour. The lower closure part 56 is arranged closer to the tool receptacle 10 than the upper closure part 54. The tool device further comprises two ball bearings 58, 60, which engage around the two closure parts 54, 56. It is in this context also conceivable that the magazine unit 24 comprises simple slide bearings instead of the ball bearings 58, 60.

Inside the magazine unit 24 the torque limitation unit 14 is arranged. The torque limitation unit 14 comprises ten torque limitation elements 16, 18, 20. The torque limitation elements 16, 18, 20 are arranged along the rotary working axle 22 successively. The torque limitation unit 14 further comprises a guiding element 62, which is arranged on an end of the torque limitation unit 14 that faces the tool receptacle 10. The guiding element 62 is embodied cylinder-shaped. The guiding element 62 comprises four longitudinal grooves into which the holding rods 46, 48, 50, 52 engage. The holding rods 46, 48, 50, 52 form a linear guidance of the guiding element 62. The guiding element 62 is supported torsionally stable with respect to the holding rods 46, 48, 50, 52.

All torque limitation elements 16, 18, 20 have an identical shape. Each torque limitation element 16, 18, 20 is arranged rotated by 90 degrees with respect to each neighboring torque limitation element 16, 18, 20. In the following, the shape of the uppermost torque limitation element 16 is described as an example. The torque limitation element 16 is embodied as a truncated cone, wherein two planar torque transmission surfaces 64, facing away from each other and extending perpendicularly to a base surface and a cover surface of the truncated cone, have been introduced in a lateral surface area. The torque transmission surfaces 64 extend in parallel to each other. The torque transmission surfaces 64 abut the holding rods 46, 48, 50, 52. The holding rods 46, 48, 50, 52 form a linear guidance of the torque limitation unit 14. The torque limitation unit 14 is supported torsionally stable with respect to the holding rods 46, 48, 50, 52.

The torque limitation elements 16, 18, 20 are embodied in a one-part implementation with each other. Precisely put, the torque limitation elements 16, 18, 20 are produced in an injection molding process. The torque limitation elements 16, 18, 20 are embodied of a plastics material. A person having ordinary skill in the art will herein use a plastic material he deems expedient, e.g. in particular polyethylene, polypropylene, polystyrene, polyester, polyvinylchloride, polyamide, polyethylene terephthalate, polyurethane or phenoplast. The guiding element 62 is arranged on a cover surface of a lowermost torque limitation element 20. To put it more precisely, the guiding element 62 is embodied in a one-part implementation with the lowermost torque limitation element 20. The lowermost torque limitation element 20 is in an operating state situated closest to the tool receptacle 10. The torque limitation elements 16, 18, 20 are arranged on the rotary working axle 22 of the tool receptacle 10. The rotary working axle 22 herein corresponds to a rotary symmetry axis with respect to which the torque limitation elements 16, 18, 20 are embodied rotationally symmetrical.

The magazine unit 24 further comprises a compression spring 66. The compression spring 66 is embodied as a screw compression spring. The compression spring 66 is made of nitinol. In this context it is also conceivable that the compression spring 66 is made of another material that is deemed expedient by the person skilled in the art, e.g. in particular a plastics material, a copper-beryllium alloy, a caoutchouc material, a fiber composite material or preferably of high-grade steel. The compression spring 66 is arranged inside an end 68 of the magazine unit 24 that faces the tool receptacle 10. The compression spring 66 is on one end supported on the lower closure part 56. On another end the compression spring 66 is supported against the guiding element 62. The guiding element 62 consequently pushes against the torque limitation elements 16, 18, 20. The compression spring 66 thus exerts a thrust force onto the torque limitation unit 14.

The tool device further comprises an operating unit 12. The operating unit 12 comprises two operating parts 30, 32. The operating parts 30, 32 form a receiving space 34, in which the torque limitation unit 14 is arranged in an assembled state. The operating parts 30, 32 are herein embodied in such a way that a non-destructive access to the receiving space 34 is avoided.

The operating parts 30, 32 are embodied as shell-type handle parts. The operating parts 30, 32 are embodied at least substantially symmetrical to each other. The operating parts 30, 32 are joined together. In the exemplary embodiment shown the operating parts 30, 32 are connected to each other by substance-to-substance bond. The substance-to-substance bond is established by an adhesive connection. It is in this context also conceivable to couple the operating parts 30, 32 with each other by a force-fit and/or form-fit connection. Herein a person having ordinary skill in the art will in particular consider a latch connection between the operating parts 30, 32. The operating parts 30, 32 are connected to each other inseparably. A non-destructive separation of the operating parts 30, 32 is thus not possible. The joined operating parts 30, 32 implement a handle. The operating parts 30, 32 are connected to outer rings of the ball bearings 58, 60 in a torsionally stable fashion. The magazine unit 24 is connected to inner rings of the ball bearings 58, 60 in a torsionally stable fashion.

The tool device further comprises a torque transmission unit 72. The torque transmission unit 72 is provided to receive respectively one of the torque limitation elements 16, 18, 20. The torque transmission unit 72 comprises a torque limitation element receptacle 70. The torque limitation element receptacle 70 forms a recess within the operating unit 12. In a plane extending perpendicularly to the rotary working axle the torque limitation element receptacle 70 is complementary in shape to the torque limitation elements 16, 18, 20. A torque limitation element 16, 18, 20 arranged inside the torque limitation element receptacle 70 is hence connected to the operating unit 12 in a torsionally stable manner.

When the tool device is used, a torque is applied onto the operating unit 12 manually. The tool receptacle 10 is coupled to the operating unit 12 via the torque limitation unit 14 in a torsionally stable manner. The tool receptacle 10 acts counter to the created torque of the operating unit 12. Thus, onto the torque limitation element 16 that is arranged in the torque limitation element receptacle 70 a torsion is applied with respect to the neighboring torque limitation element 18. The torque limitation unit 14 is arranged between the operating unit 12 and the tool receptacle 10. The torque transmission unit 72 is provided to exert a force onto the torque limitation element 16 when a torque is transmitted from the operating unit 12 to the tool receptacle 10.

The torque limitation element 16 arranged in the torque transmission unit 72 is provided to be destroyed when a given torque is exceeded. In other words, the torque transmission unit 72 destroys the received torque limitation element 16 when the given torque is exceeded. Herein the received torque limitation element 16 is separated off the neighboring torque limitation element 18. The separating-off is effected via the torsion between the received torque limitation element 16 and the neighboring torque limitation element 18. The operating unit 12 then rotates freely about the tool receptacle 10 by approximately a quarter turn.

The operating unit 12 further comprises a receiving chamber 28. The receiving chamber 28 is provided to receive destroyed torque limitation elements 16, 18, 20 of the torque limitation unit 14. The receiving chamber 28 is delimited by the two operating parts 30, 32 of the operating unit 12. The off-separated and hence destroyed torque limitation element 16, 18, 20 is moved into the receiving chamber 28 by a gravitation force and/or by the thrust force. By way of the quarter turn of the operating unit 12 about the tool receptacle 10, the previously neighboring torque limitation element 18 engages into the torque limitation element receptacle 70. The thrust force of the compression spring 66 thus introduces the previously neighboring torque limitation element 18 into the torque transmission unit 72. The operating unit 12 is thus once again coupled in a torsionally stable manner with respect to the tool receptacle 10 until the given torque is reached. This is continued until the lowermost torque limitation element 20 is separated off the guiding element 62. Afterwards the tool device is non-usable and has to be disposed of. All off-separated torque limitation elements 16, 18, 20 are then arranged loosely within the receiving chamber 28. The torque limitation unit 14 is thus provided to irreversibly interrupt a torque transmission between the operating unit 12 following a limited number of torque excess events.

As has been mentioned above, following each torque excess event the compression spring 66 moves another torque limitation element 18, 20 into the torque transmission unit 72 until the lowermost torque limitation element 20 has been separated off the guiding element 62. Herein the compression spring 66 relaxes. Consequently the spring force of the compression spring 66 decreases. A friction force between the torque limitation unit 14 and the magazine unit 24 acts counter to the spring force. For keeping the thrust force at least substantially constant despite a relaxation of the compression spring 66, the magazine unit 24 comprises a compensation unit 26. The compensation unit 26 is provided to keep the thrust force at least substantially constant for each torque limitation element 16, 18, 20. The compensation unit 26 comprises a friction-setting unit. The friction-setting unit comprises four surfaces diverging from one another, which are implemented by the holding rods 46, 48, 50, 52. The surfaces depart from the tool receptacle 10 by approximately 0.1 mm towards the torque limitation unit 14. To achieve a constant thrust force, a person having ordinary skill in the art will in this context set a divergence he considers expedient. It is in this context also conceivable that the person having ordinary skill in the art will provide a spring-setting unit that is configured for setting the spring force of the compression spring 66.

The tool device comprises a pass-through channel 36. The pass-through channel 36 penetrates the tool receptacle 10, the operating unit 12 and the torque limitation unit 14 completely. The pass-through channel 36 is embodied cylinder-shaped. A symmetry axis of the pass-through channel 36 is located on the rotary working axle 22. The pass-through channel 36 has a smaller diameter than the torque limitation unit 14. The pass-through channel 36 is free of bends. Guiding the torque limitation unit 14 through the pass-through channel 36 is thus avoided. The pass-through channel 36 is provided to guide a Kirschner wire. The pass-through channel 36 herein has a diameter of less than 1 mm.

The tool device further comprises a filling level indication unit 38. The filling level indication unit 38 is provided to indicate a remaining number of torque limitation elements 16, 18, 20. For this purpose the filling level indication unit 38 comprises an indication recess 74. The indication recess 74 extends slit-like in an operating part 32 of the operating parts 30, 32. As an alternative, the filling level indication unit 38 extends in both operating parts 30, 32. The indication recess 74 runs in parallel to the rotary working axle 22. The indication recess 74 is provided for an optical check of a filling level of the magazine unit 24. A width of the indication recess 74 is less than 3 mm. Guiding the torque limitation unit 14 through the indication recess 74 is avoided. The filling level indication unit 38 further comprises a numeralization. The numeralization comprises the numerals 1 to 10. The numerals are allocated to the respective torque limitation elements 16, 18, 20.

The invention claimed is:
1. A hand-held tool device, for use in a surgical method, comprising:
   a tool receptacle;
   an operating unit;
   a torque limitation unit;
   a torque transmission unit; and
   a magazine unit; wherein
   the torque limitation unit is arranged between the operating unit and the tool receptacle and includes a plurality of torque limitation elements, which are configured to be destroyed when a given torque is exceeded,
   the magazine unit exerts a thrust force onto the torque limitation elements for introducing them one by one into the torque transmission unit,
   the torque limitation unit is configured to receive each of the torque limitation elements to destroy it when the given torque is exceeded,
   the torque limitation elements are arranged on a rotary working axle of the tool receptacle, and
   the operating unit comprises at least one receiving chamber provided to receive at least one destroyed torque limitation element of the torque limitation unit.

2. The tool device as claimed in claim 1, wherein the operating unit comprises at least one operating part for forming a receiving space in which the torque limitation unit is arranged in an assembled state.

3. The hand-held tool device as claimed in claim 1, wherein the torque limitation unit is provided to irreversibly interrupt torque transmission between the operating unit and the tool receptacle following a limited number of torque excess events.

4. The hand-held tool device as claimed in claim 1, wherein the torque limitation elements are embodied in a one-part implementation with each other.

5. The hand-held tool device as claimed in claim 1, wherein the torque transmission unit is provided to destroy each torque limitation element by torsion.

6. The hand-held tool device as claimed in claim 1, wherein the magazine unit includes a compensation unit, which is configured to keep the thrust force at least substantially constant for each of the torque limitation elements.

7. The hand-held tool device as claimed in claim 1 further comprising a pass-through channel, which passes through at least a major part of the tool receptacle, the operating unit, and the torque limitation unit.

8. The hand-held tool device as claimed in claim 1 further comprising a filling level indication unit, which indicates a remaining number of torque limitation elements.

9. A hand-held tool device, for use in a surgical method, comprising:
a tool receptacle;
an operating unit;
a torque limitation unit;
a torque transmission unit; and
a magazine unit; wherein
the torque limitation unit is arranged between the operating unit and the tool receptacle and includes a plurality of torque limitation elements, which are configured to be destroyed when a given torque is exceeded,
the magazine unit exerts a thrust force onto the torque limitation elements for introducing them one by one into the torque transmission unit,
the torque limitation the torque limitation unit is configured to receive each of the torque limitation elements to destroy it when the given torque is exceeded,
elements are arranged on a rotary working axle of the tool receptacle, and
the hand-held tool device further comprises a pass-through channel penetrating the tool receptacle, the operating unit and the torque limitation unit at least to a major part.

10. The hand-held tool device as claimed in claim 9, wherein the torque limitation unit is provided to irreversibly interrupt torque transmission between the operating unit and the tool receptacle following a limited number of torque excess events.

11. The hand-held tool device as claimed in claim 9, wherein the torque limitation elements are embodied in a one-part implementation with each other.

12. The hand-held tool device as claimed in claim 9, wherein the torque transmission unit is provided to destroy each torque limitation element by torsion.

13. The hand-held tool device as claimed in claim 9, wherein the magazine unit includes a compensation unit, which is configured to keep the thrust force at least substantially constant for each of the torque limitation elements.

14. The hand-held tool device as claimed in claim 9, wherein the operating unit comprises at least one operating part for forming a receiving space in which the torque limitation unit is arranged in an assembled state.

15. The hand-held tool device as claimed in claim 9 further comprising a filling level indication unit, which indicates a remaining number of torque limitation elements.

16. A hand-held tool device, for use in a surgical method, comprising:
a tool receptacle;
an operating unit;
a torque limitation unit;
a torque transmission unit; and
a magazine unit; wherein
the torque limitation unit is arranged between the operating unit and the tool receptacle and includes a plurality of torque limitation elements, which are configured to be destroyed when a given torque is exceeded,
the magazine unit exerts a thrust force onto the torque limitation elements for introducing them one by one into the torque transmission unit,
the torque limitation unit is configured to receive each of the torque limitation elements to destroy it when the given torque is exceeded,
the torque limitation elements are arranged on a rotary working axle of the tool receptacle, and
the hand-held tool device further comprises a filling level indication unit provided to indicate a remaining number of torque limitation elements.

17. The hand-held tool device as claimed in claim 16, wherein the torque limitation unit is provided to irreversibly interrupt torque transmission between the operating unit and the tool receptacle following a limited number of torque excess events.

18. The hand-held tool device as claimed in claim 16, wherein the torque limitation elements are embodied in a one-part implementation with each other.

19. The hand-held tool device as claimed in claim 16, wherein the torque transmission unit is provided to destroy each torque limitation element by torsion.

20. The hand-held tool device as claimed in claim 16, wherein the magazine unit includes a compensation unit, which is configured to keep the thrust force at least substantially constant for each of the torque limitation elements.

* * * * *